(12) United States Patent
Peyman (10) Patent No.: US 6,702,853 B1
(45) Date of Patent: Mar. 9, 2004

(54) INTRAOCULAR LENS SYSTEM UTILIZING AN ADHESIVE AND METHOD FOR IMPLANTING THE SAME

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 59 days.

(21) Appl. No.: 09/676,503

(22) Filed: Oct. 2, 2000

(51) Int. Cl.[7] ................................................. A61F 2/16
(52) U.S. Cl. ..................... 623/6.39; 623/6.12; 623/6.37
(58) Field of Search ............... 623/6.39, 6.11, 623/6.12, 6.16, 6.36, 6.37, 6.38

(56) References Cited

U.S. PATENT DOCUMENTS

| | | | |
|---|---|---|---|
| 5,002,571 A | * 3/1991 | O'Donnell, Jr. et al. | 623/6 |
| 5,098,444 A | 3/1992 | Feaster | 623/6 |
| 5,133,748 A | * 7/1992 | Feaster | 623/6 |
| 5,282,851 A | * 2/1994 | Jacob-LaBarre | 623/6 |
| 5,755,786 A | 5/1998 | Woffinden et al. | 623/15 |
| 6,013,101 A | * 1/2000 | Israel | 623/6.37 |
| 6,066,138 A | 5/2000 | Sheffer et al. | 606/49 |
| 6,197,057 B1 | 3/2001 | Peyman et al. | 623/6.32 |
| 6,231,603 B1 | * 5/2001 | Lang et al. | 623/6.37 |

OTHER PUBLICATIONS

Jane E. Henney, MD, "Surgical Sealant for Lung Cancer", JAMA, Aug. 9, 2000–vol. 284, No. 6, p. 685.

* cited by examiner

Primary Examiner—David H. Willse
Assistant Examiner—Javier G Blanco
(74) Attorney, Agent, or Firm—Roylance, Abrams, Berdo & Goodman, LLP (57) ABSTRACT

A system and method for removing cataract cells inside of a lens capsule of an eye and inserting into the lens capsule an intraocular lens having an adhesive applied to at least one of its surface. Preferably, the adhesive is applied to the surface of the intraocular lens that faces the cornea of the eye. The adhesive causes the lens to adhere to an interior portion of the lens capsule, such as the remaining epithelial layer. The lens capsule conforms or shrinks around the intraocular lens, removing substantially any space between the lens capsule and the intraocular lens. Since there is no room between the lens capsule and the intraocular lens, proliferation of the remaining cells will not occur and therefore capsular opacification is eliminated or substantially reduced. Additionally, since the lens capsule and the intraocular lens are coupled together, the intraocular lens can move when ciliary body muscles contract and therefore, the focal point of the eye can change as in a normal eye.

25 Claims, 6 Drawing Sheets

ёш...

INTRAOCULAR LENS SYSTEM UTILIZING AN ADHESIVE AND METHOD FOR IMPLANTING THE SAME

CROSS-REFERENCE TO RELATED APPLICATIONS

Related subject matter is disclosed in copending U.S. Patent Application of Gholam A. Peyman entitled "System and Method for Thermally and Chemically Treating Cells at Sites of Interest in the Body to Impede Cell Proliferation", Ser. No., 09/494,248, filed on Jan. 31, 2000, and in copending U.S. Patent Application of Gholam A. Peyman entitled "System and Method for removing Cataract or Other Cells in an Eye Using Water Jet and Suction", Ser. No. 09/597,737, filed on Jun. 19, 2000, the entire contents of both of which are incorporated herein by reference.

FIELD OF INVENTION

The present invention relates to a system and method for treating and removing cells in an interior chamber of an eye, such as in the lens capsule of an eye, and implanting an intraocular lens. More particularly, the present invention relates to a system and method that treats cataract by killing and removing the cataract causing cells from the interior of the lens of the eye without or substantially without causing protein denaturation to occur in the cells, and then inserting an intraocular lens having an adhesive thereon into the lens capsule of the eye so that the adhesive secures the intraocular lens to the lens capsule to eliminate capsular opacification and enable focusing.

BACKGROUND OF THE INVENTION

Cataract is a condition that creates cloudiness in the lens of an eye, and is one of the major causes of blindness in the developing world. Cataract occurs in the lens of an eye and impedes the lens from focusing light on the retina. The lens is composed of tightly packed lens fibers surrounded by a collagenous elastic capsule. Beneath the lens capsule are epithelial cells, which are responsible for the metabolic function of the lens. Cataract may occur in any or all of these parts of the lens, which results in several different classifications of cataract, namely, subcapsular, cortical, and nuclear. To treat cataract, the cloudy portion of the lens, whether it is in the lens fibers, the epithelial, or both, or in any other portion of the lens, should be surgically removed. Generally, this is attempted by making an incision in the corneal periphery (limbus) to enter the anterior chamber and remove the cataract.

A conventional method for removing cataract in the eye is the (manual) extracapsular technique. In this procedure, the eye is opened at the limbus, and either a bent needle or any other curved sharp edged instrument or special forceps are employed to open the anterior lens capsule and remove the nucleus within the capsule of the lens. Thereafter, the remaining cortical material is removed so as to leave a clear posterior lens capsule in the eye. An artificial lens is then inserted into the lens capsule. The lens capsule therefore provides a barrier between the anterior chamber and the vitreous cavity of the eye, as well as a resting surface for the implanted artificial lens. However, this method does not stop cells from proliferating and causing capsular opacification.

Other types of cell removing techniques, such as phacoemulsification, use a probe containing an ultrasonic wave generator, a rinsing fluid and a suction tip. In the phacoemulsification technique, an incision is made in the cornea of an eye and the probe is inserted. Compacted proteins of the lens nucleus are broken up by ultrasonic power and are emulsified by a rinsing fluid. The emulsified lens proteins as well as soft peripheral lens proteins are removed from the eye by the suction tip. Phacoemulsification is generally considered superior to extracapsular surgery because it only requires a surgical wound of about 2–3 millimeters as opposed to about 7 millimeters for extracapsular surgery. However, the problem with phacoemulsification is that opacification of the remaining capsule or posterior capsular opacification can occur. This opacification is caused by proliferation of the remaining lens epithelium, which this procedure has failed to remove from the remaining capsule entity. An example of this type of technique is disclosed in U.S. Pat. No. 6,066,138 to Sheffer et al., the entire contents of which are incorporated herein by reference.

Each of the above-identified methods provide techniques for removing the interior portion of the lens and inserting an intraocular lens therein. However, in these conventional methods, the lens simply rests in the lens capsule, loosely fitting around the lens so that a space exists between the interior of the lens capsule, such the epithelial layer, and the intraocular lens. Due to this space, proliferation and opacification of the remaining lens cells may occur.

Additionally, when the eye attempts to focus at objects that are close, such as within one meter, by changing the shape or position of the lens, the intraocular lens implanted according to the conventional methods discussed above does not move with the lens capsule. Specifically, when the interior portion of the lens is removed, the ciliary muscles which are attached to the lens capsule via zonular fibers all around the lens remain attached to the exterior of the loose lens capsule. The insertion of an intraocular lens does not tighten the zonules, and they thus remain slack. As one side of the zonules or ropes move or is tightened, the zonules on the other side stay loose. Therefore, the movement or tightening of the zonules does not move the implanted intraocular lens. Thus, the intraocular lens is unable to change the focal point of the eye and a patient will likely require a second lens, such as eyeglasses or contact lenses, to focus on objects that are close. Using a secondary lens only allows the patient to focus at a specific distance and the patient would need a lens having a different refractive index to focus at any other distance.

Thus, there is a continuing need to improve the systems and methods for removing cataract and preventing unwanted cell proliferation in the eye, while also improving the focusing ability of the intraocular lens systems.

SUMMARY OF THE INVENTION

Accordingly, it is an object of the present invention to provide a system and method for removing cells from an eye, such as cells in the lens capsule, and inserting an intraocular lens in such a manner to eliminate or substantially reduce posterior capsular opacification.

Another object of the present invention is to provide a system and method for inserting an intraocular lens, utilizing adhesive, into the lens capsule to eliminate space between the lens and the lens capsule, and therefore eliminate or substantially reduce capsular opacification.

Still another object of the present invention is to provide a system and method for inserting an intraocular lens, utilizing adhesive, into the lens capsule that attaches the intraocular lens to the lens capsule, making it possible to change the focal point of the eye by enabling the intraocular lens to move with the lens capsule when ciliary muscle contracts so that the eye can focus on objects that are close.

The foregoing objects are basically obtained by providing an intraocular lens system, comprising a lens having a first surface and a second surface, and adapted to be inserted into the a lens capsule of an eye. An adhesive is disposed on a portion of at least one of the first and second surfaces of the lens, and is adapted to attach the intraocular lens to an interior portion of the lens capsule.

The foregoing objects are further obtained by providing a method for implanting an intraocular lens into an interior of a lens of an eye. The method comprises the steps of making an incision in the eye, and then removing a portion of the interior of the lens while leaving at least the lens capsule intact. An adhesive is then applied to a surface of the intraocular lens, and the intraocular lens is inserted into the interior of the lens, so that the adhesive attaches the intraocular lens to an interior portion thereof.

Other objects, advantages and novel features of the invention will become apparent from the following detailed description, which, taken in conjunction with the annexed drawings, disclose preferred embodiments of the invention.

BRIEF DESCRIPTION OF THE DRAWINGS

Referring to the drawings which form a part of this disclosure.

DETAILED DESCRIPTION OF THE PREFERRED EMBODIMENT

Figure 1:
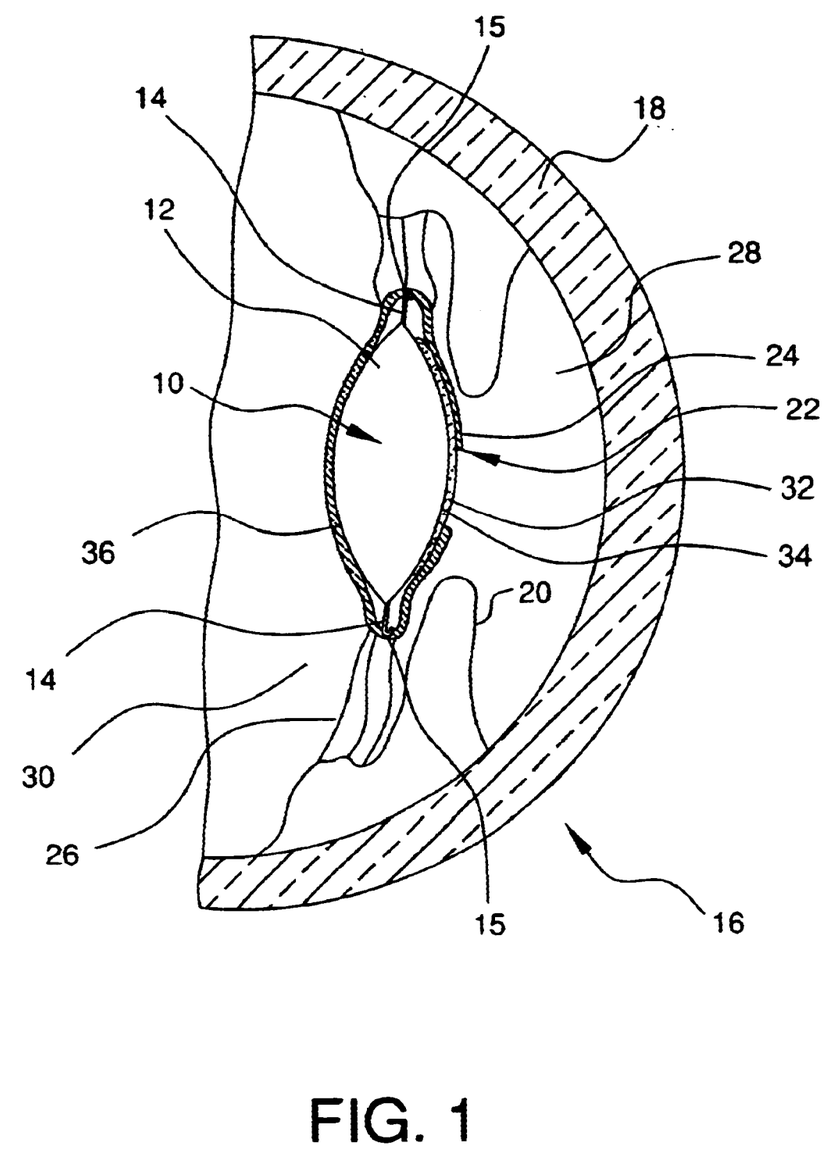
FIG. 1 illustrates an intraocular lens system, utilizing adhesive, according to an embodiment of the present invention, which is inserted into the lens capsule of an eye shown in cross-section.

As initially shown in FIG. 1, an embodiment of the present invention provides an intraocular lens system (IOL) 10 having a lens portion 12 and haptics 14. As described in detail below, the lens system 10 is adapted to be inserted into an eye 16 having a cornea 18, iris 20, lens 22, lens capsule 24, zonular ligaments or zonules 26 and anterior 28 and posterior 30 chambers, and the IOL 10 is attached to the lens capsule 24 using an adhesive 32.

The lens portion 12 preferably is a conventional lens as is known in the art and has a front or first surface 34 and a rear or second surface 36. The lens portion 12 may be convex, concave, or any other shape that can correct for any vision disorders in the eye 16. For example, the lens portion 12 may be shaped such that it alleviates conditions such as myopia, hyperopia or astigmatism, or may be any combination of different lenses either combined into one lens system or separate lens systems that would alleviate any combination of the aforementioned problems. Different types of multiple lens systems are described in U.S. patent application Ser. No. 09/397,036 to Peyman et al. entitled "Glare-Free Intraocular Lens and Method for Using the Same" filed Apr. 20, 2000, and U.S. patent application Ser. No. 09/187,739 to Peyman et al. entitled "Lens Conversion System for Teledioptic or Defractive Configurations" filed Oct. 27, 1998, the entire contents of both of which are incorporated herein by reference.

The haptics 14 are adapted to couple to the lens portion 12 as is known in the art, and to couple the lens position 12 to the interior portion of the lens capsule 24. Haptics 14 are preferably rigidly attached to lens portion 12, but may be hinged, allowing the lens portion 12 to move relative to at least a portion of the haptics 14. Haptics 14 preferably extend from the lens portion 12 and have U-shaped hooks 15 that are adapted to pierce the interior of the lens capsule 24, coupling the lens system 10 thereto. Additionally, haptics 14 may be any type of connecting device. Different types of haptics are described in U.S. patent application Ser. No. 09/397,036 to Peyman et al. identified above. However, the IOL 10 does not necessarily require haptics 14 to couple to the lens capsule 24, and may simply be placed inside the lens capsule 24 without haptics 14.

Figure 2:
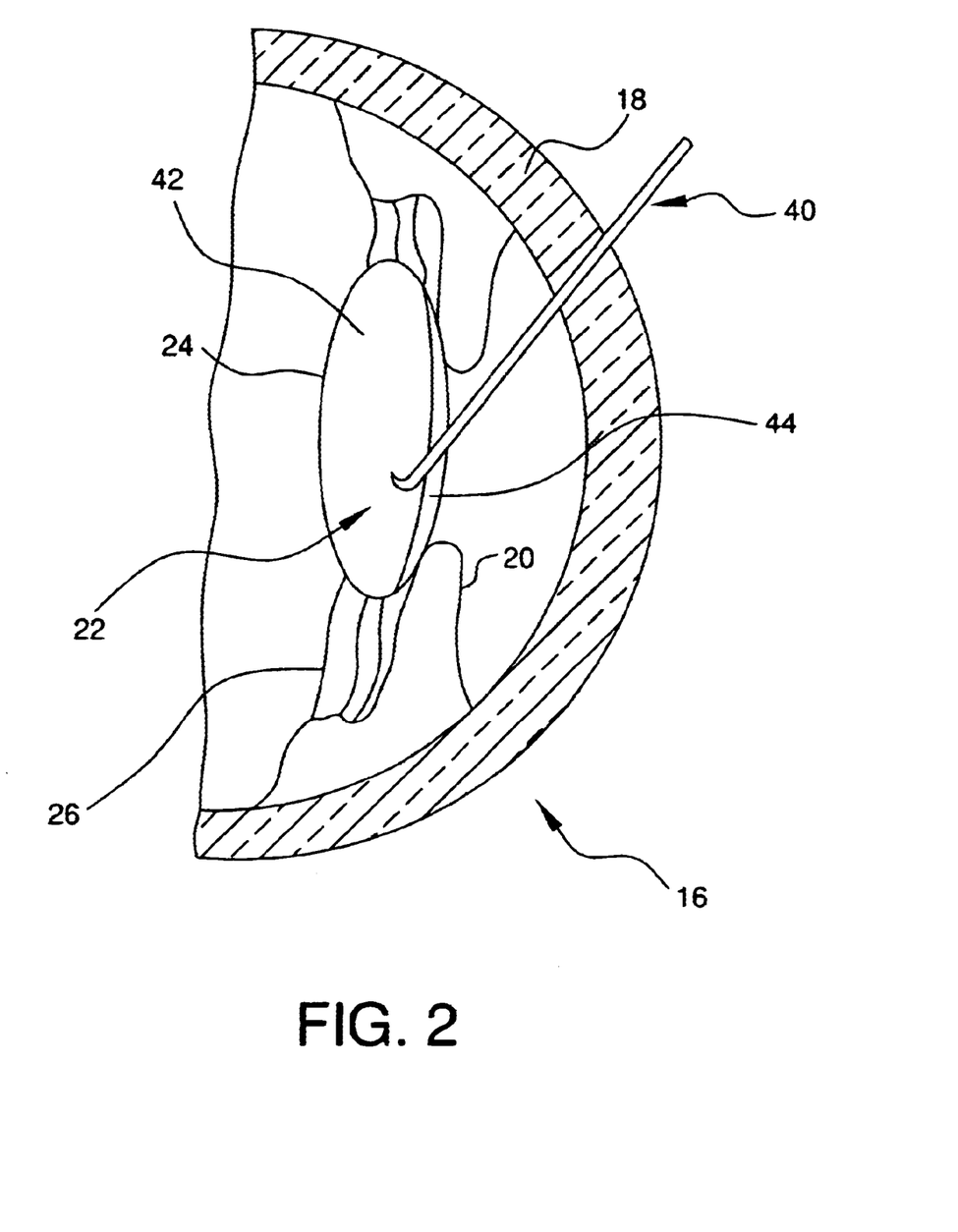
FIG. 2 illustrates the use of a device to remove the interior portion of an eye shown in cross-section.

An example of a method in which the IOL 10 is implanted in the lens capsule 24 according to an embodiment of the present invention will now be described. As shown in FIG. 2, the interior of the lens 22 is removed using a device 40, as is known in the art, or by any conventional method. Generally, all or a portion of the lens fiber 42 and/or epithelial layer 44 of the lens capsule is removed. Different methods suitable for removing the appropriate portions of the lens are described in U.S. Patent Applications of Ser. No. 09/494,248, and Ser. No. 09/597,737, referenced above.

Figure 3:
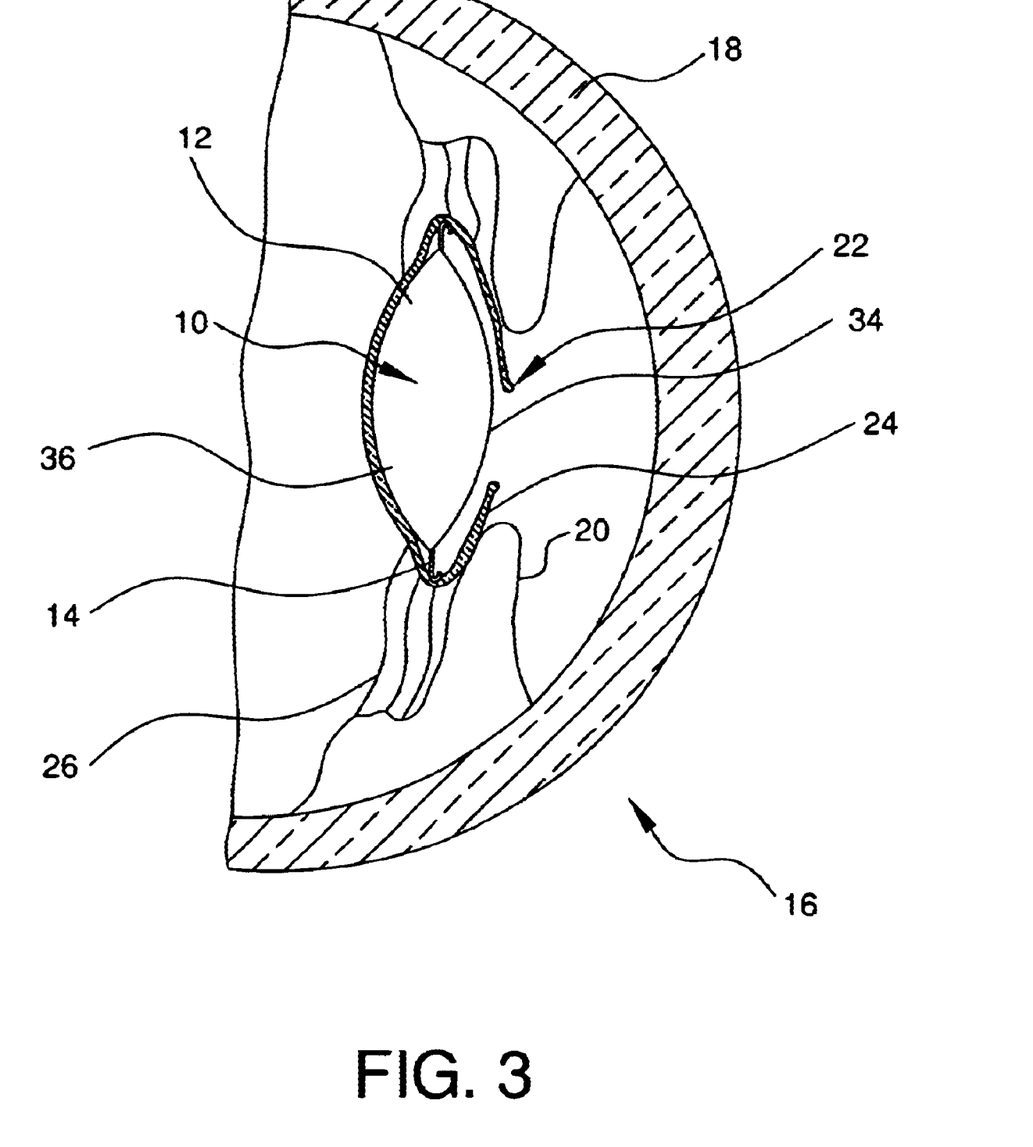
FIG. 3 is a cross-sectional view of the intraocular lens system of FIG. 1, prior to the addition of the adhesive.

The IOL 10 is then inserted into the interior portion of the lens capsule 24, with the haptics 14 attaching thereto. Preferably, the entire IOL 10 is inserted in the lens capsule 24. However, a portion of IOL 10 may not be inserted into or be enclosed by the lens capsule 24 if so desired. It is preferable to apply adhesive 32 to the IOL 10 or to the interior of the lens capsule 24 prior to inserting the IOL 10 in the lens capsule, but the adhesive may be applied after insertion of the IOL 10. Haptics 14 attach to the interior of the lens capsule 24 and help hold the IOL 10 in place, as shown in FIG. 3. Adhesive 32 on the front surface 34 of the lens portion attaches the lens portion 12 to the lens capsule 24.

Figure 4:
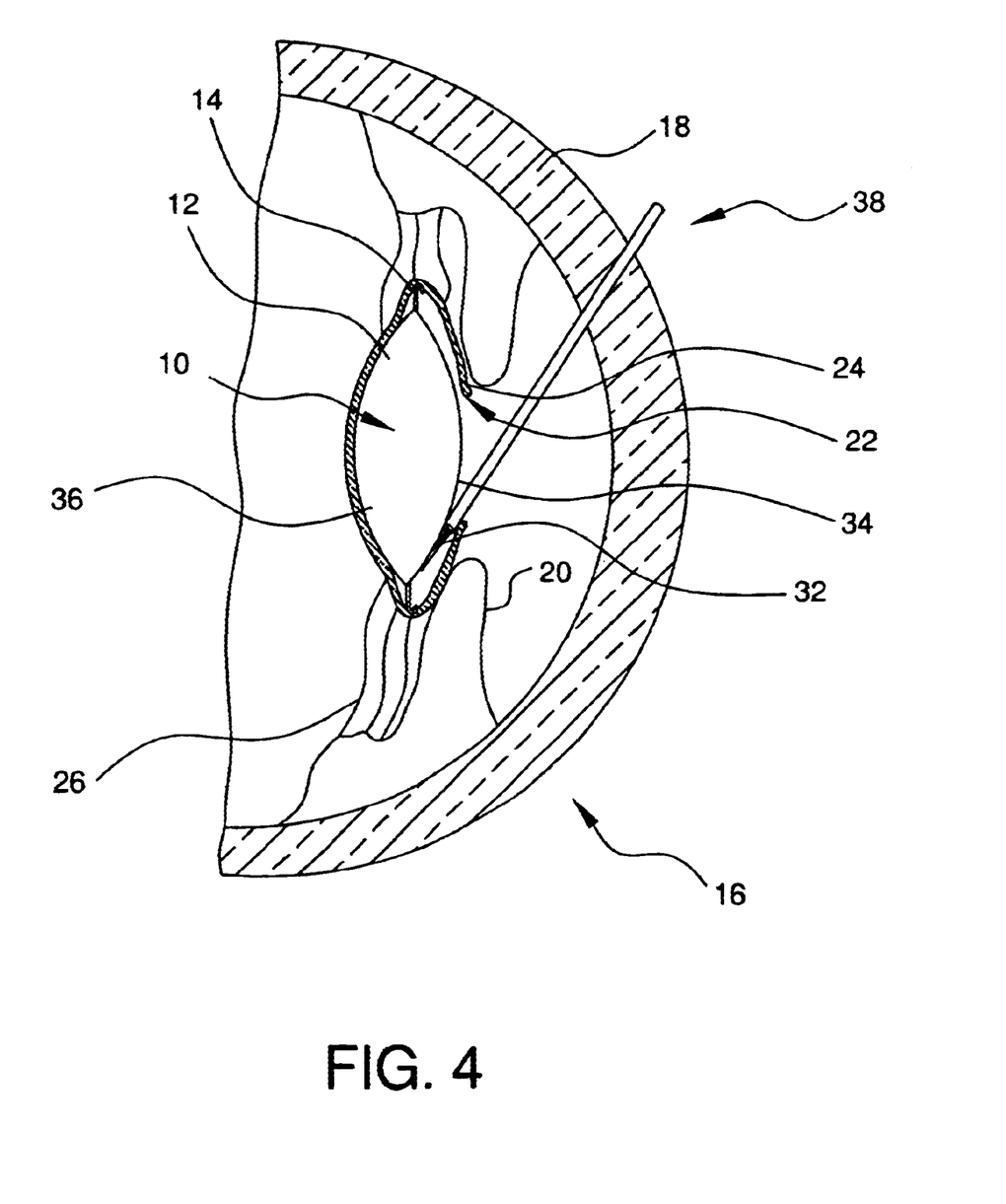
FIG. 4 is a cross-sectional view of the eye and intraocular lens system as shown in FIG. 3, with the adhesive being added.

Adhesive 32 is preferably a liquid thermobond, such as cyanoacrylate or hydrogel. More particularly, adhesive 32 can be FocalSeal-L, which is a synthetic absorbable sealant and primer solution. Upon exposure to blue-green light, the primer and sealant solutions polymerize to form a cross-linked, clear flexible, adherent hydrogel network. However, the adhesive may be any biodegradable or nonbiodegradable substance suitable for implantation in the eye 16. Most nonbiodegradable substances will not degrade a significant amount due to the lack of space between the IOL 10 and the lens capsule 24. The adhesive 32 may be applied to the lens portion 12 prior to the IOL 10 being inserted into the eye, during implantation or after the IOL 10 is inserted into eye 16 using a device 38, as shown in FIG. 4. The device 38 is adapted to fit inside of the lens capsule 24 and inject or apply an adhesive to either or both the front and the rear surfaces of the IOL 10. The liquid adhesive 32 fills the space between the IOL 10 and the lens capsule 24, and gels or hardens to thus fix the IOL 10 to the inside of the lens capsule 24. The adhesive may be applied to the peripheral part of the lens.

Figure 6:
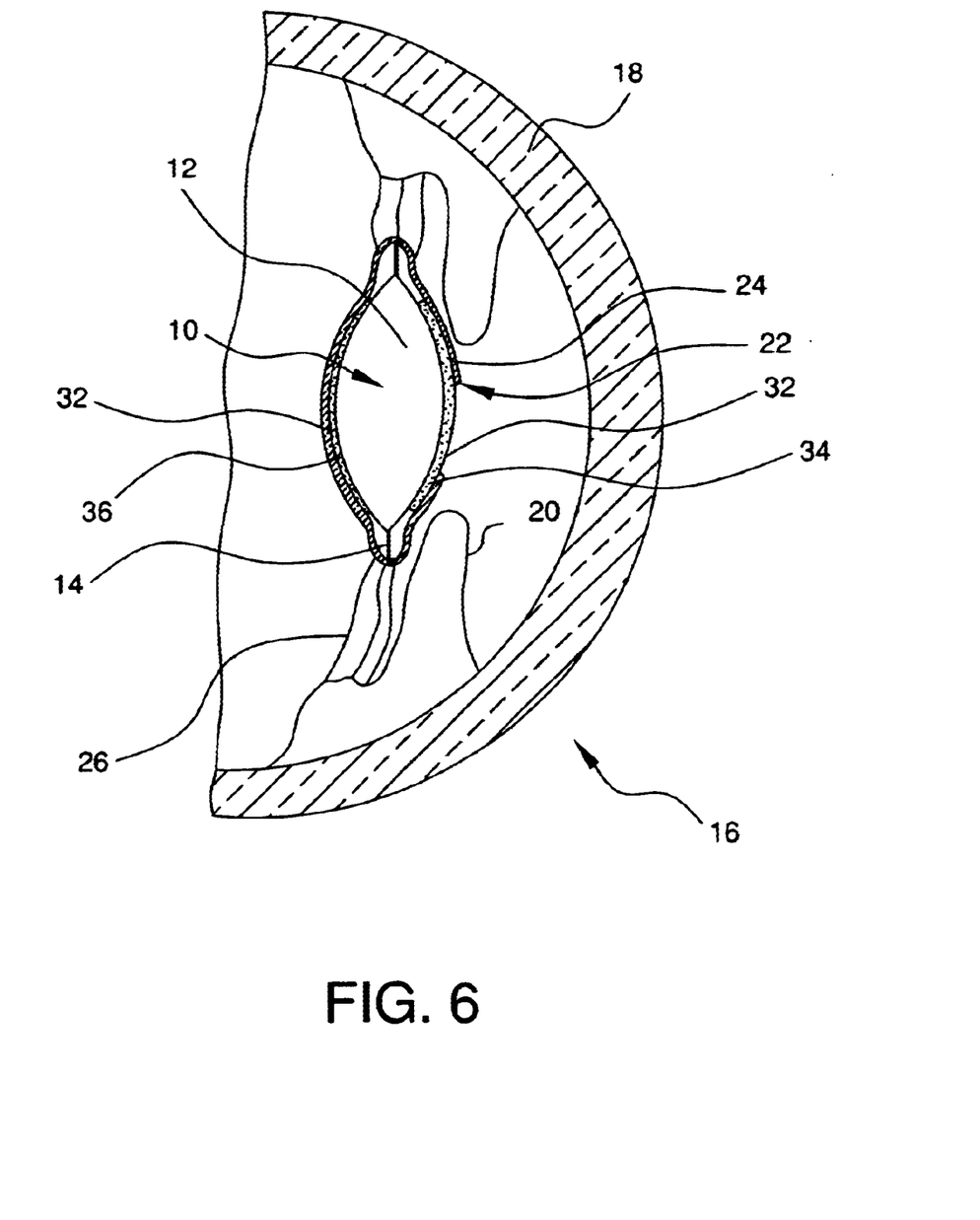
FIG. 6 is a cross sectional view of the eye and intraocular lens system as shown in FIG. 1, with adhesive applied on both the front and rear surfaces of the intraocular lens.

As shown in FIG. 1, the lens capsule 24 adheres to and conforms around the lens portion 10. By adhering the lens portion as described, there is no space or substantially no space between the lens portion 12 and the lens capsule 24. Thus, there is no room for the cells to grow and proliferate, and capsular opacification will therefore not occur. Preferably, there is no need to apply adhesive 32 to the rear surface 36 of the lens as the lens capsule 24 will be stretched around IOL 10 and not allow any or substantially any room for cell proliferation. However, it is possible to apply adhesive 32 to second surface 36, thus the lens capsule conforms or shrinks around the entire lens portion, as shown in FIG. 6.

Figure 5:
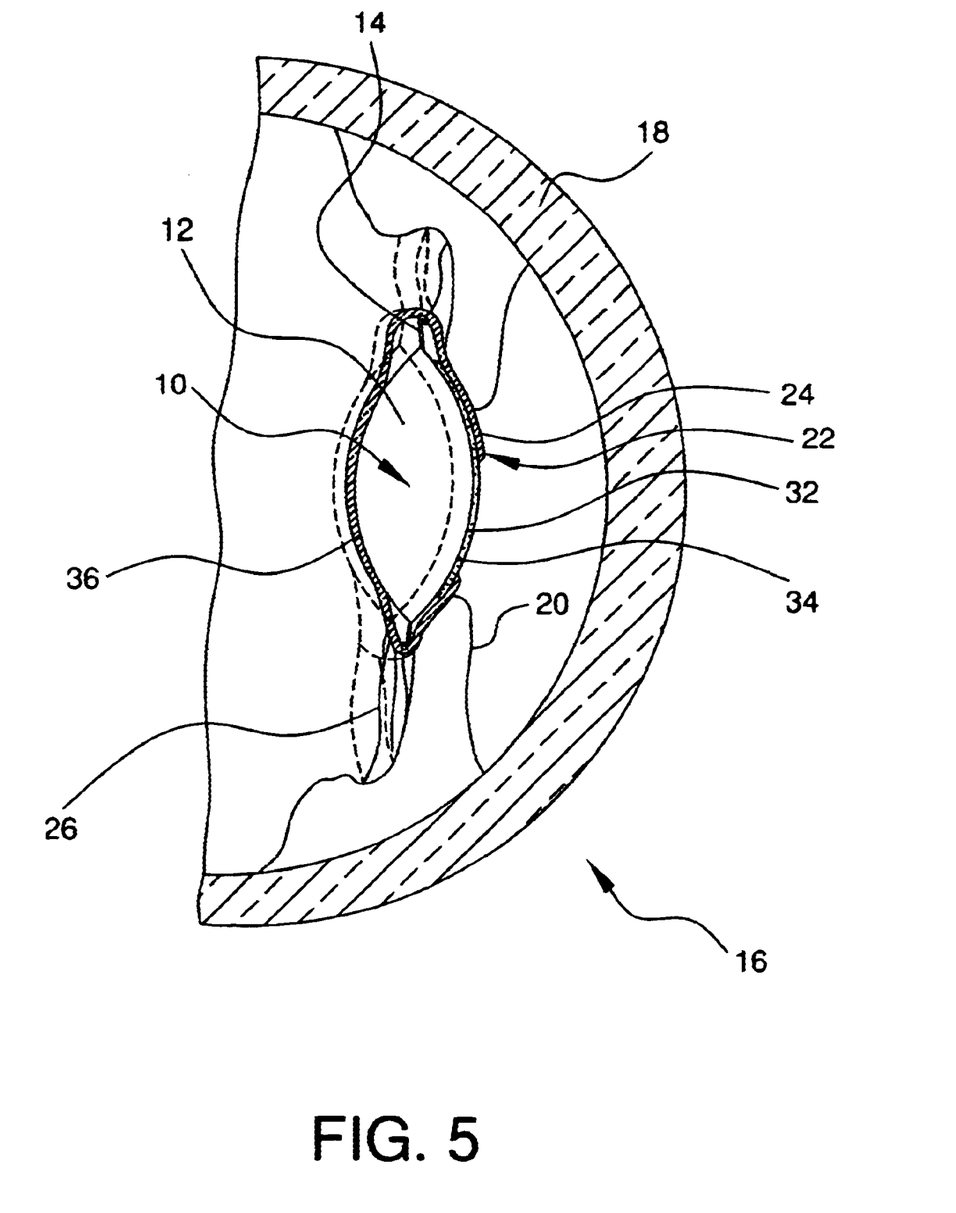
FIG. 5 is a cross sectional view of the eye and intraocular lens system as shown in FIG. 1, further illustrating the lens capsule and intraocular lens system moving forward due to tightening of the zioners.

Additionally, by having the lens portion 12 attached to the lens capsule 24, IOL 10 will move when lens capsule 24 moves. That is, as discussed above, the lens capsule 24 conforms or shrinks around the IOL 10 as the adhesive gels or solidifies, which causes zioners 26 to also become tight. Hence, when one side of the zonules 26 tightens or moves due to contraction of ciliary muscle or a change in vitreous pressure, the zonules 26 on the other side tighten or move as well. As shown in FIG. 5, since the zonules 26 are attached around lens capsule 24, when they tighten or loosen, the lens capsule 24 moves forward or backward, changing the focal point of the lens.

In the embodiment of the present invention, movement of the lens capsule 24 forces IOL 10 to move with lens capsule 24. In FIG. 5, the moved positions of the IOL 10, lens capsule 24 and zonules 26 are shown in solid lines, and the original positions of IOL 10, lens capsule 24, and zonules 26 are shown with dotted lines. This movement of the IOL 10 is about 1 millimeter and causes a change in refractive power of up to approximately +3 diopters, or a focusing ability of up to about 33 centimeters from the patient. In other words, the present invention allows the eye to automatically focus on objects that are in range of distance from the eye of about 33 centimeters to infinity. This change in refractive power or accommodation enables a patient to focus on objects that are close, such as when a patient is reading, without the use of a secondary lens, such as eyeglasses or contact lenses. It does not alter the patient's ability to focus on objects that are far away, since the ciliary muscles and zonular ligaments are generally tight when focusing on objects that are far away and the lens does not need to accommodate for objects outside of about one meter from the patient. By adhering the IOL 10 to lens capsule 24, the patient may therefore focus in a similar manner as a person with a natural lens.

In addition, IOL may have haptics 14 rigidly coupled to the lens portion 12 as shown in FIGS. 1 and 5, so that the entire IOL moves with the lens capsule, or the IOL may have no haptics or haptics that are hinged, allowing the lens portion 12 to move relative to the haptics. The hinged haptics would allow the lens portion to move a greater distance than the outer portion of the haptics and thus allow a larger diopter change.

While specific embodiments have been chosen to illustrate the invention, it will be understood by those skilled in the art that various changes and modifications can be made therein without departing from the scope of the invention as defined in the appended claims.

What is claimed is:

1. An intraocular lens system, comprising
a lens portion having a first surface and a second surface, and being adapted for insertion into a lens capsule of an eye, the eye having a central optical axis; and
an adhesive, disposed on a portion of said first surface of said lens portion at an area generally proximal to the central optical axis, and being adapted to attach said first surface of said lens portion to an interior, front portion of the lens capsule;
said lens portion being further adapted to move and change the refractive power of the lens system.

2. A system according to claim 1, wherein
said lens portion is adapted to be inserted substantially completely within said lens capsule.

3. A system according to claim 1, wherein
said lens portion is adapted to substantially fill the interior of said lens capsule.

4. A system according to claim 1, wherein
said adhesive attaches said first surface of said lens portion to an epithelial layer of said lens capsule.

5. A system according to claim 1, further comprising
said adhesive is disposed on said second surface of said lens, and is further adapted to attach said second surface of said lens portion to a portion of said lens capsule.

6. A system according to claim 1, wherein
said first and second surfaces of said lens portion are on substantially opposite sides of said intraocular lens.

7. A system according to claim 1, further comprising
at least one haptic adapted to couple said lens portion to a portion of the eye.

8. A system according to claim 7, wherein
said at least one haptic includes a hinged portion.

9. A system according to claim 1, wherein
said adhesive includes at least one of a liquid thermobond, cyanoacrylate, hydrogel or FocalSeal-L.

10. A system according to claim 1, wherein
said adhesive is disposed on said second surface, such that said lens capsule shrinks around said lens portion, causing zonules in the eye to become tight.

11. A method for implanting an intraocular lens into an interior of a lens of an eye, the lens having a lens capsule and lens fiber, the method comprising the steps of:
removing a portion of the lens fiber in the interior of the lens, leaving the lens capsule at least substantially intact,
applying adhesive to a first surface of the intraocular lens at an area generally proximal to the central optical axis of the eye,
inserting the intraocular lens into the interior of the lens capsule, and
allowing the adhesive to attach the intraocular lens to an interior, front surface of the lens capsule, in such a manner so that the intraocular lens is adapted to move and change its refractive power and the refractive power of the lens.

12. A method according to claim 11, wherein
the inserting step includes inserting the intraocular lens so that the adhesive attaches the first surface to an interior epithelial layer of the lens.

13. A method according to claim 11, wherein
the applying adhesive step further includes applying said adhesive to a second surface of the intraocular lens.

14. A method according to claim 13, wherein
the inserting step includes inserting the intraocular lens so that the adhesive attaches the second surface to an interior portion of the lens capsule.

15. A method according to claim 11, wherein the applying the adhesive step includes applying the adhesive to the surface of the intraocular lens before said intraocular lens is inserted into the lens capsule in the inserting step.

16. A method according to claim 11, wherein the applying the adhesive step includes applying the adhesive to the surface of the intraocular lens after said intraocular lens is inserted into the lens capsule in the inserting step.

17. A method according to claim 11, further comprising the step of forming an incision and removing the lens fiber through the incision.

18. A method according to claim 11, wherein the applying the adhesive step includes applying at least one of a liquid thermobond, cyanoacrylate, hydrogel or FocalSeal-L.

19. A method according to claim 11, wherein the inserting step includes attaching a haptic coupled to the intraocular lens to a portion of the eye.

20. A system according to claim 1, wherein said adhesive is applied to at least a portion of the lens portion that intersects the main optical axis of the eye.

21. A system according to claim 20, wherein said adhesive is applied to substantially all of said first surface of said lens portion.

22. A method according to claim 11, further comprising the step of exposing the adhesive to laser light after the intraocular lens has been implanted to adhere the intraocular lens to the lens capsule.

23. A method according to claim 11, wherein the applying adhesive step includes applying the adhesive to at least a portion of the intraocular lens that intersects the main optical axis of the eye.

24. A method according to claim 23, wherein the applying adhesive step includes applying the adhesive to substantially all of said first surface of said intraocular lens.

25. A method according to claim 11, further comprising the step of allowing the adhesive to attach the intraocular lens to an interior, back surface of the lens capsule such that the lens capsule shrinks around the intraocular lens, causing zonules in the eye to become tight.

* * * * *